US008648115B2

(12) United States Patent
Arnold et al.

(10) Patent No.: US 8,648,115 B2
(45) Date of Patent: Feb. 11, 2014

(54) ANTI-OOMYCETES

(75) Inventors: Norbert Arnold, Halle (DE); Axel Teichert, Bern (CH); Sabine Rosahl, Halle (DE); Bernhard Westermann, Halle (DE); Ludger Wessjohann, Halle (DE); Lennart Eschen-Lippold, Halle (DE); Tobias Draeger, Demker (DE)

(73) Assignees: BASF SE, Ludwigshafen (DE); Leibniz-Institute Fuer Pflanzenbiochemie, Halle (DE)

( * ) Notice: Subject to any disclaimer, the term of this patent is extended or adjusted under 35 U.S.C. 154(b) by 67 days.

(21) Appl. No.: 13/321,997

(22) PCT Filed: May 26, 2010

(86) PCT No.: PCT/EP2010/003189
§ 371 (c)(1),
(2), (4) Date: Feb. 6, 2012

(87) PCT Pub. No.: WO2010/136185
PCT Pub. Date: Dec. 2, 2010

(65) Prior Publication Data
US 2012/0129938 A1    May 24, 2012

(30) Foreign Application Priority Data
May 26, 2009  (DE) .......................... 10 2009 022 619

(51) Int. Cl.
*A61K 31/20*     (2006.01)
(52) U.S. Cl.
USPC ........................................................ 514/560

(58) Field of Classification Search
USPC .......................................................... 514/560
See application file for complete search history.

(56) References Cited

FOREIGN PATENT DOCUMENTS

WO      WO 0042853 A1 *   7/2000

OTHER PUBLICATIONS

International Search Report in International Application No. PCT/EP2010/003189, filed May 26, 2010.
English language translation of the International Preliminary Report on Patentability from corresponding International Application No. PCT/EP2010/003189, filed May 26, 2010.
Eschen-Lippold, Lennart, et al., "Antioomycete Activity of γ-oxocrotonate Fatty Acids against *P. infestans*", Journal of Agricultutal and Food Chemistry, 2009, p. 9607-9612, vol. 57.
Teichert, Axel, et al. "Unusual Bioactive4-oxo-2-alkenoic Fatty Acids from *Hygrophorus eburneus*", Zeitschrift fur Naturforschung, Teil B: Anorganische chemie, Organische Chemie, Verlag der Zeitschrift fur Naturforschung. Tubingen, DE, Jan. 2005, p. 25-32, vol. 60, No. 1.
Tilo Lübken, "Hygrophorone neue antifungische Cyclopentenonderivate aus Hygrophorus-Arten (Basidimycetes)", Dissertation Martin-Luther__Universitat Halle-Wittenberg, [online], Mar. 2006, Seiten 1-130 XP007916032 Gefunden im Internet: URL:http://sundoc.bibliothek.uni-halle.de/diss-online/06/06H309/prom.pdf>.

* cited by examiner

*Primary Examiner* — Kevin E Weddington
(74) *Attorney, Agent, or Firm* — Brinks Gilson & Lione

(57) ABSTRACT

The present invention relates to the use of compounds of general formula (I) or of a salt thereof as anti-oomycetes and to a method for combating plant pathogens using said compounds.

20 Claims, 6 Drawing Sheets

ANTI-OOMYCETES

Figure 1:
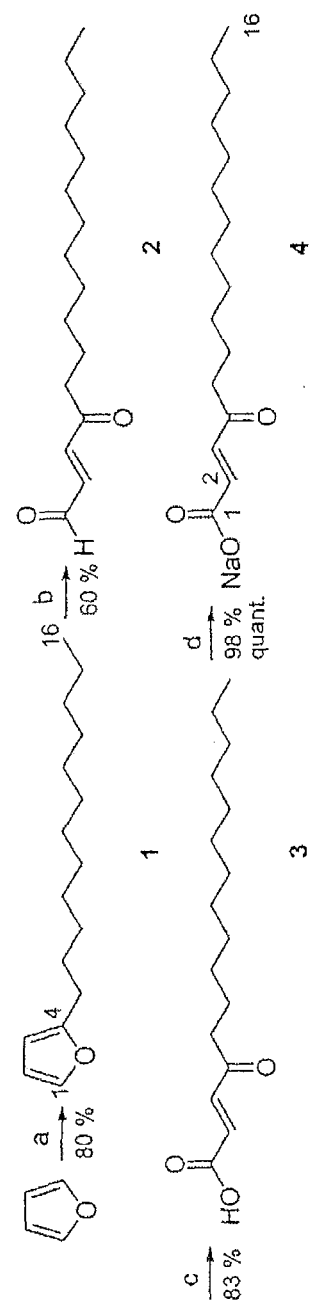

This application is a National Stage application of International Application No. PCT/EP2010/003189 filed May 26, 2010, the entire contents of which is hereby incorporated herein by reference. This application also claims priority under 35 U.S.C. §119 to German Patent Application No. 10 2009 022 619.2, filed May 26, 2009, the entire contents of which is hereby incorporated herein by reference.

The present invention relates to the use of the compounds of the general formula (I) or of a salt thereof as antioomycotic, and to a method for controlling plant pathogens in which these compounds are used.

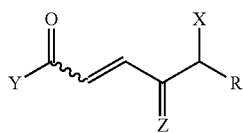

(I)

The class of the oomycetes or Peronosporomycetes (formally referred to as Oomycota or Oomycetes), which do not belong to the fungi (Fungi), comprises a varied group of saprophytic and pathogenic species. The latter include not only species which infect animals or microorganisms, but also devastating plant pathogens. Important plant pathogens are found in the genera *Albugo, Bremia, Plasmopara, Peronospora* and *Phytophthora*. These obligat-pathogenic species cause, for example, diseases such as white rust or downy mildew in a range of different plants. Within the genus *Phytophthora*, there are described more than 60 different species which infect predominantly dicotyledonous plants. Many of them are highly adapted to a specific host, or to a few hosts, while others are capable of colonizing many different plants.

*Phytophthora infestans*, the causative organism of late blight of tomato, or late blight of potato, is considered the most destructive plant pathogen worldwide. Infections are difficult to control and can lead to total yield losses since the life cycle of *P. infestans* only takes a few days.

Most traditional fungicides are ineffective against *P. infestans* and other oomycetes. The reason therefor is the lack of typical fungal target structures for the activity of many fungicides in the Peronosporomycetes.

The present invention is therefore based on the object of providing novel effective agents against plant pathogens, in particulari Peronosporomycetes.

This object is achieved by the embodiments of the present invention which are characterized in the claims.

According to the invention, there is provided in particular the use of compounds of the general formula (I) as antioomycotic, and a method of controlling plant pathogens in which these compounds are used.

Accordingly, one subject matter of the present invention relates to the use of a compound of the formula (I) or a salt thereof as antioomycotic:

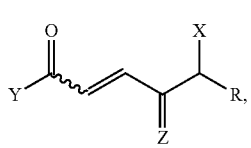

(I)

in which

X is selected from among H, $OR^1$, $SR^1$, $NR^1R^{2+}$, $N(OR^1)(R^2)$, $N(R^1)$—$NR^1NR^2$ or $N(R^1R^2R^3)^+A^-$, Y is selected from among $OR^1$, $O^-Cat^+$ or $NR^1R^2$, Z is selected from among O, S, $NR^1$, $NOR^1$, N—CN or N—$NR^1R^2$, R represents a substituent selected from the group consisting of (i) an unsubstituted or mono- or polysubstituted ($C_3$-$C_{22}$)-alkyl radical, (ii) an unsubstituted or mono- or polysubstituted ($C_3$-$C_{22}$)-alkenyl radical, (iii) an unsubstituted or mono- or polysubstituted ($C_3$-$C_{22}$)-alkynyl radical, (iv) an unsubstituted or mono- or polysubstituted —$(CH_2)_m$-spermine radical, (v) an unsubstituted or mono- or polysubstituted —$(CH_2)_m$-spermidine radical, (vi) an unsubstituted or mono- or polysubstituted N-methylated —$(CH_2)_m$-sperm(id)ine radical, where m is in each case an integer from 1 to 4 and where the one or the plurality of substituents in the above-mentioned radicals (i) to (vi) can be selected independently of one another from among group α, consisting of a ($C_1$-$C_6$)-alkyl radical, a ($C_1$-$C_6$)-thioalkyl radical, a ($C_3$-$C_7$)-cycloalkyl radical which can have one or more hetero atoms such as, for example, O or S, a ($C_1$-$C_6$)-alkoxy radical, a hydroxyl group, a trifluoromethyl group, a triazole group, bromine, chlorine, fluorine, an unsubstituted, mono- or disubstituted phenyl, phenoxy, benzyl, benzyloxy, naphthyl or naphthoxy radical, and (vii) an ethyleneoxy group selected from among:

—$CH_2[OCH_2CH_2]_n$—OH,
—$CH_2[OCH_2CH_2]_n$—OMe,
—$CH_2$—$CH_2$—$[OCH_2CH_2]_n$—OH
—$CH_2$—$CH_2$—$[OCH_2CH_2]_n$—OMe
—$CH_2$—$CH_2$—$CH_2$—$[OCH_2CH_2]_n$—OH
—$CH_2$—$CH_2$—$CH_2$—$[OCH_2CH_2]_n$—OMe
—$CH_2$—$CH_2$—$CH_2$—$CH_2$—$[OCH_2CH_2]_n$—OH or
—$CH_2$—$CH_2$—$CH_2$—$CH_2$—$[OCH_2CH_2]_n$—OMe, where n=1-20, preferably n=1-5, $R^1$, $R^2$ and $R^3$ independently of one another are selected from among hydrogen, a ($C_1$-$C_6$)-acyl radical, —$CONH_2$, —(CO)—$(CH_2)_{0-6}$—COOH, a lactyl radical, a ($C_1$-$C_6$)-alkyl radical, a ($C_3$-$C_7$)-cycloalkyl radical which can have one or more hetero atoms such as, for example, O or S, an unsubstituted, mono- or disubstituted phenyl, benzyl or naphthyl radical whose substituents can be selected from among group α, $A^-$ represents an anion selected from among halide, chlorate or carboxylate, $Cat^+$ represents a cation, in particular monovalent or divalent cations such as, for example, alkali metal cations ($Na^+$, $K^+$), alkaline-earth metal cations ($Ca^{2+}$, $Mg^{2+}$) or quaternary ammonium cations, the stereoisomeric center at C5, if present, is present in the R or S form or as a racemate, and the C2-C3 double bond is present in the E or Z form, preferably the E form (trans).

A further subject matter of the present invention relates to a method of controlling plant pathogens, comprising the application of an effective amount of one of the above-defined compounds or of a salt thereof to a plant, a part of the plant or the soil in which the plant grows. The method according to the invention can be used both preventatively and curatively.

In this context, the expression "plant pathogens" comprises all phytopathogenic fungi, protists, bacteria and viruses.

In a preferred embodiment of the present invention, the plant pathogens are fungi (Fungi). Especially preferred plant pathogens in this context are *Colletotrichum coccodes, Colletotrichum graminicola, Septoria tritici, Fusarium graminearum, Blumeria graminis, Magnaporthe grisea, Ustilago maydis, Alternaria solani, Cladosporium fulvum,*

*Cochliobolus heterostrophus, Pyrenophora tritici-repentis, Verticillium albo-atrum* and *Verticillium dahliae*.

In a further preferred embodiment of the present invention, the plant pathogens are oomycetes (Peronosporomycetes, formally referred to as Oomycota or Oomycetes). Especially preferred in this context are oomycetes from among the genera *Albugo, Bremia, Plasmopara, Peronospora* and *Phytophthora*. An especially preferred plant pathogen from the genus *Peronospora* is *Peronospora manshurica*. Especially preferred plant pathogens from among the genus *Phytophthora* are *Phytophthora sojae, Phytophthora palmivora, Phytophthora ramorum, Phytophthora cinnamomi, Phytophthora capsici* and *Phytophthora infestans*. Very especially preferred in this context is *Phytophthora infestans*.

In a preferred embodiment of the present invention, the plants which are protected or treated with the method according to the invention are from the group consisting of the Fabaceae, in particular *Glycine max*; the Cucurbitaceae, in particular *Cucurbita* spp. such as *Cucurbita pepo, Cucumis* spp. such as *Cucumis melo* and *Cucumis sativus*, and *Citrullus* spp. such as *Citrullus lanatus*; the Brassicaceae, in particular *Brassica* spp. such as *Brassica napus, Brassica oleracea* and *Brassica rapa*; the Poaceae, in particular *Triticum* spp., *Hordeum* spp., *Oryza sativa* and *Zea mays*; the Solanaceae, in particular *Nicotiana* spp. such as *Nicotiana tabacum, Capsicum* spp. such as *Capsicum annuum*, and *Solanum* spp. such as *Solanum tuberosum, Solanum lycopersicum* and *Solanum melongena; Vitis* spp. such as *Vitis vinifera; Beta vulgaris*; and *Theobroma cacao*. Very especially preferred in this context is *Solanum tuberosum*.

Furthermore, the method according to the invention can be used for protecting or treating trees, in particular Coniferae, in particular Pinaceae, and ornamentals, in particular ornamental plants.

The concentration of the compound or of the salt thereof in the method according to the invention ranges from 1 nM to 10 nM, preferably from 10 nM to 1 mM. Especially preferred is a concentration of 100 μM.

Methods of applying, to a plant or parts of the plant, an effective amount of one of the above-defined compounds or a salt thereof are known to those skilled in the art and comprise, for example, spraying, atomizing, painting or dipping the plant.

In an especially preferred embodiment of the method according to the invention, the compounds according to the invention are present in the form of a mixture in combination with a carrier, in which mixture the active compound is present in an amount of between 0.1 and 99% by weight, preferably between 1 and 75% by weight, based on the mixture. Mixtures in combination with a carrier, for the direct use or application to the field, comprise the compounds according to the invention in an amount of between 0.0001 and 5% by weight, preferably between 0.001 and 3% by weight, based on the mixture. The method according to the invention comprises the use of formulations and compositions, which comprise mixtures of a dispersible carrier, such as a dispersible inert finely-divided solid carrier and/or a dispersible liquid carrier, such as an inert organic solvent and/or water, preferably with the inclusion of an effective amount of a surface-active carrier adjuvant and an amount of the active compounds according to the invention of between 0.0001 and 99% by weight, preferably between 0.001 and 90% by weight, preferably between 0.1 and 75% by weight. The active compounds according to the invention can be applied by customarily used methods, for example as hydraulic sprays of large amounts of liquid, sprays with low amounts of liquid, ultra-low-volume sprays, by high-pressure liquid injection, slit injection, blast-air spray, air spray or dust.

A preferred embodiment of the present invention relates to the use of a compound of the formula (I) or a salt thereof as antioomycotic, where, in formula (I), X is selected from among H, $OR^1$, $NR^1R^2$, $N(OR^1)(R^a)$, $N(R^1)$—$NR^1R^2$ or $N(R^1r^2R^3)^+A^-$, Y is selected from among $OR^1$ or $O^-Cat^+$, Z is selected from O, R represents a substituent selected from the group consisting of an unsubstituted or mono- or polysubstituted $(C_3-C_{22})$-alkyl radical, preferably $(C_7-C_{12})$-alkyl radical, an unsubstituted or mono- or polysubstituted $(C_3-C_{22})$-alkenyl radical, —$CH_2[OCH_2CH_2]_n$—OH or —$CH_2[OCH_2CH_2]_n$—OMe, where n=1-20, preferably n=1-5, $R^1$, $R^2$ and $R^3$ independently of one another are selected from among hydrogen, a $(C_1-C_6)$-acyl radical or a $(C_1-C_6)$-alkyl radical and the C2-C3 double bond is present in the E form.

If the radical R represents a $(C_3-C_{22})$-alkenyl radical, then one to three double bonds can preferably be present. The double bonds can be present in the E or in the Z form. In particular, it is possible for oligoprenyl radicals to be present, which, in turn, can optionally be substituted by one or more substituents from among group α. Examples which may be mentioned in this context are geranyl, neryl, farnesyl and geranylgeranyl.

An especially preferred embodiment of the present invention relates to the use of (E)-4-oxohexadec-2-enoic acid (formula (II)) or salts thereof, in particular alkali metal salts, as antioomycotic.

(II)

A further subject matter of the present invention relates to the use of one of the compounds according to the invention or a salt thereof as disinfectant for agricultural and/or horticultural machinery.

The figures show:

FIG. 1: Synthesis of sodium (E)-4-oxohexadec-2-enoate starting from furan. (a) Furan, THF, n-BuLi (1.1 eq.) at 0° C., 30 min, then $C_{12}H_{25}Br$ (1.0 eq.) at −40° C., warm to RT; (b) 1, NBS (1.1 eq.), $NAHCO_3$ (2.0 eq.), acetone/$H_2O$ (10:1), −15° C., 1 h, pyridine (2.0 eq.); (c) 2, $NaClO_2$ (1.2 eq.), $Me_2C$=CHME (10 eq.), t-BuOH, $H_2O$, HCl, 2 h at RT; (d) 3, THF, NaOH (1.0 eq.), RT, 30 min.

Figure 2:
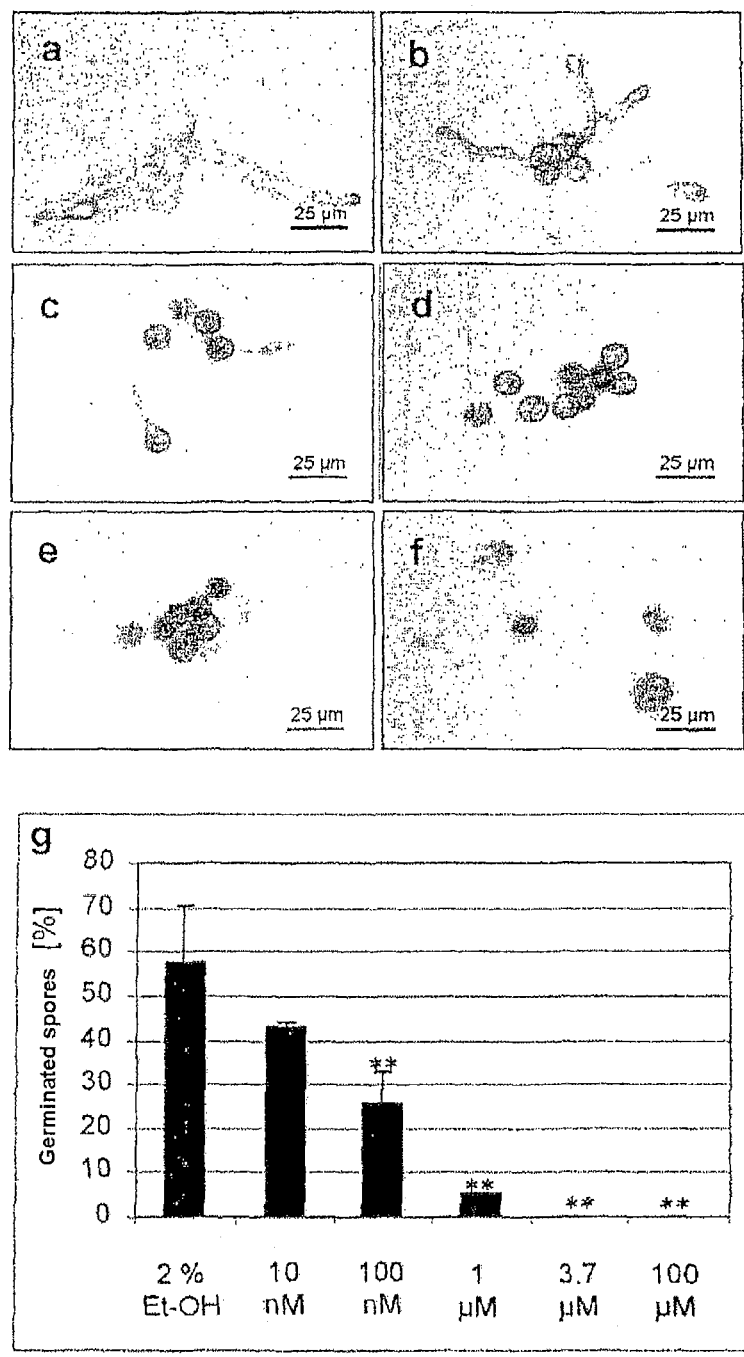

FIG. 2: The germination of *Phytophthora infestans* spores is inhibited by (E)-4-oxohexadec-2-enoic acid. Suspensions of *P. infestans* spores were treated with different dilutions of (E)-4-oxohexadec-2-enoic acid. (a) to (f) show representative phenotypes of spores in different (E)-4-oxohexadec-2-enoic acid concentrations; (a) 2% EtOH, (b) 10 nM, (c) 100 nM, (d) 1 μM, (e) 3.7 μM (f) 100 μM. The germation rates were calculated after 24 h (g). The diagram shows combined data of two independent experiments (** denotes significant differences at p<0.01; one-way ANOVA).

Figure 3:
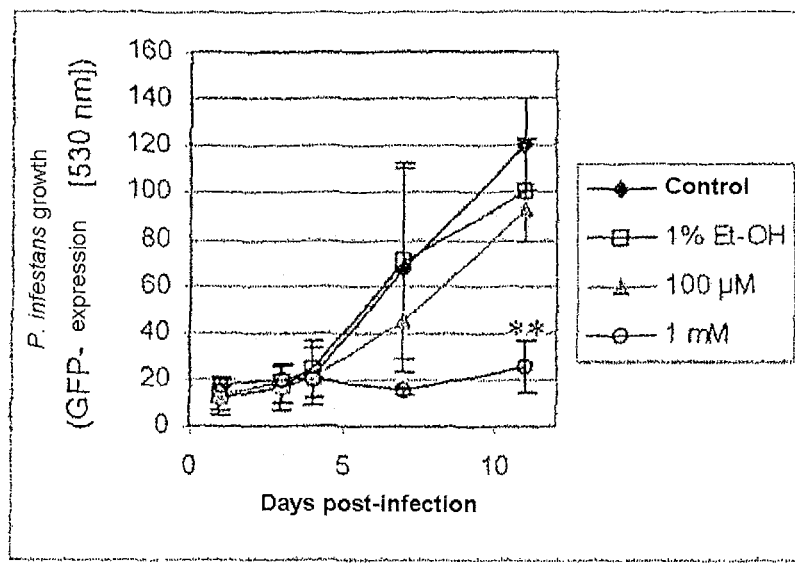

FIG. 3: Inhibitory effect of (E)-4-oxohexadec-2-enoic acid on the mycelial growth of *P. infestans*. A one-day old mycelium was inoculated with different (E)-4-oxohexadec-2-enoic acid concentrations. The growth of *P. infestans* was determined by measuring the GFP fluorescence. The graphs show combined data of two independent experiments (** denotes significant differences at p<0.01; one-way ANOVA).

Figure 4:
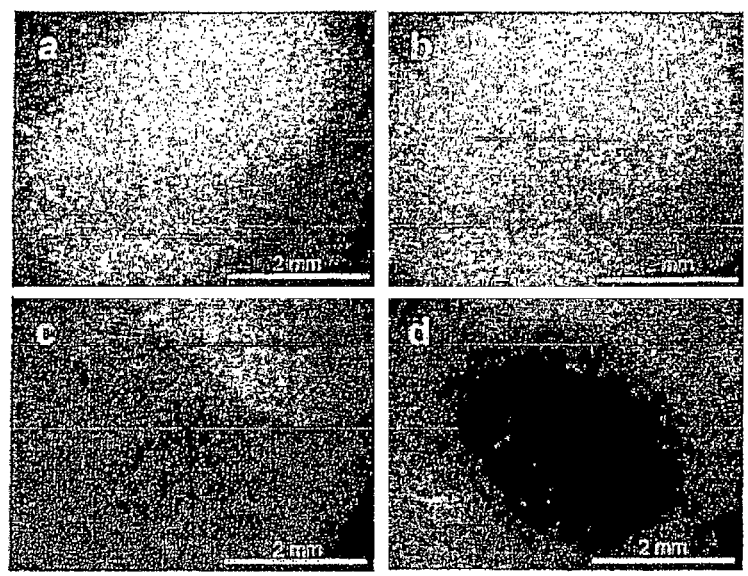
Figure 5:
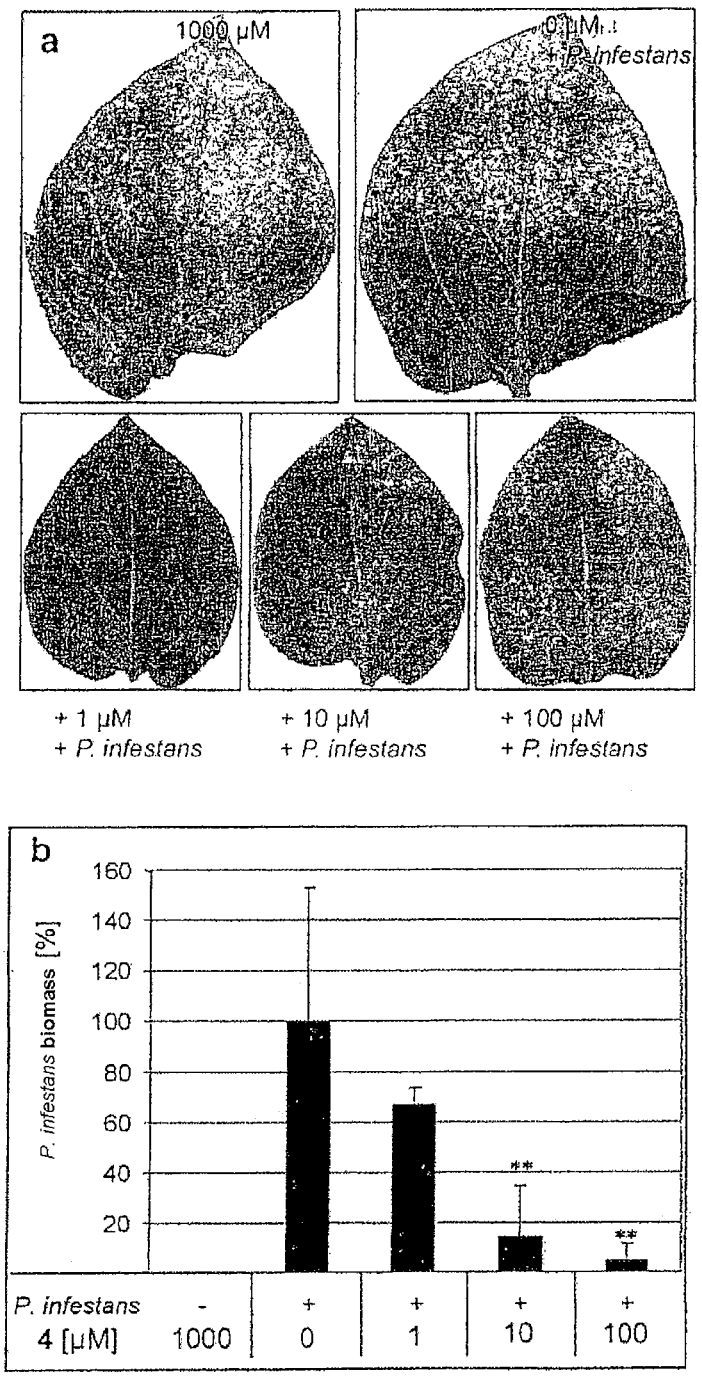
Figure 6:
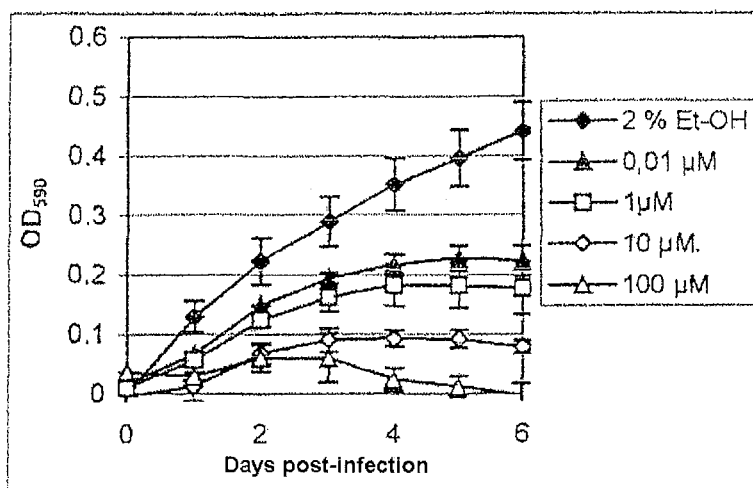

FIG. 4: Damaging effects of (E)-4-oxohexadec-2-enoic acid on established *P. infestans* mycelium. *P. infestans* was grown for 21 days on oat/bean agar in Petri dishes. Then, drops (10 µl) of (E)-4-oxohexadec-2-enoic acid in different concentrations were pipetted onto the mycelium. Antioomycetal activity resulted in damage to the mycelium, as demonstrated by the loss of GFP fluorescence. Images of representative treated locations of the mycelium were recorded 24 h after treatment with (E)-4-oxohexadec-2-enoic acid, using a fluorescence stereomicroscope. (a) Untreated, (b) 1 μM, (c) 10 μM, (d) 100 μM.

FIG. 5: Infections with *P. infestans* were inhibited to a high degree by spraying plants with sodium (E)-4-oxohexadec-2-enoate (4). 2 h before inoculation with a *P. infestans* zoo spore solution, the abaxial leaf surface of 21-day old plants was sprayed with sodium (E)-4-oxohexadec-2-enoate. (a) Phenotype of treated leaves; (b) determination of the *P. infestans* biomass of infected leaf material 3 d post-infection. The controls used were uninfected samples sprayed with 1000 μM of sodium (E)-4-oxohexadec-2-enoate and infected, unsprayed samples (** denotes significant differences at $p<0.01$; one-way ANOVA).

FIG. 6: Inhibitory effect of (E)-4-oxohexadec-2-enoic acid on the mycelial growth of *Colletotrichum coccodes*. One-day old mycelium in 96-well plates was inoculated with different (E)-4-oxohexadec-2-enoic acid concentrations. The growth of *C. coccodes* was determined by measuring the $OD_{590}$. The experiment was repeated twice, with identical results. At the end of the experiment, the statistical analysis showed highly significant differences between the treatment with 2% EtOH and all tested concentrations of (E)-4-oxohexadec-2-enoic acid ($p<0.01$; one-way ANOVA).

The present invention is illustrated in greater detail with reference to the following nonlimiting examples.

Materials and Methods:

General Aspects.

All reagents and solvents were analytical-grade or were purified with the aid of standard methods. The melting points were determined via standard methods using hotstage microscopy (Leica DM LS2) and not corrected. The reactions were monitored by means of thin-layer chromatography on silica gel 60 $F_{254}$ (Merck, 0.040-0.063 mm) and detected using UV light or molybdatophosphoric acid. The solutions were concentrated under reduced pressure at 40° C. The column chromatography was performed on silica gel 60 (Merck, 0.063-0.200 mm). The $^{1}H$ (300 or 400 MHz) and $^{13}C$ (75.5 or 100.5 MHz) NMR spectra were recorded at room temperature (RT) using VARIAN Mercury spectrometers. For 2-dodecylfuran and (E)-4-oxohexadec-2-enal, the chemical shifts were referenced to internal TMS (δ=0 ppm, $^{1}H$) or $CDCl_3$ (δ=77.0 ppm, $^{13}C$). Deuterated ethanol was used as the solvent for (E)-4-oxohexadec-2-enoic acid. The chemical shifts were referenced to the signals of the internal solvent methyl groups (δ=1.11 ppm, $^{1}H$, or δ=17.2 ppm, $^{13}C$). Positive and negative ESI and APCI mass spectra were obtained by an API 150Ex (Applied Biosystems) equipped with a turbo ion source. Highly-resolved positive and negative ESI mass spectra were obtained by a Bruker Apex 70e FT-ICR mass spectrometer (Bruker Daltonics) which was equipped with an Infinity™ cell, a 7.0 Tesla superconducting magnet (Bruker) an rf-only hexapole ion guide and an external electrospray ion source (Agilent). *P. infestans* isolate 208 m2 was grown on oat-bean medium (3.4% by weight bean flour, 1.7% by weight oat flour, 0.85% by weight sucrose, 1.5% by weight Bacto-Agar, 5 μg/ml geneticin). Measurements of GFP-emitted light were performed with the aid of a Cytofluor II plate reader (Millipore; excitation 485 nm, emission 530 nm). GFP fluorescence images were recorded using a Leica MZ FLIII fluorescence stereomicroscope (Leica Microsystems). An MRX Plate Reader 1.12 (Dynatech Laboratories) was used for measuring the *P. infestans* biomass. Quantitative PCR was performed as described.

Reagents and Solvents.

Tetrahydrofuran (THF), n-butyllithium (n-BuLi), furan, sodium hydroxide, HCl, pyridine, N-bromosuccinimide (NBS), 2-methyl-2-butene, $NaClO_2$ and dodecyl bromide were obtained from conventional laboratory suppliers.

Synthesis of the Compounds

2-Dodecylfuran (FIG. 1, 1). An ice-cold solution of furan (5.34 ml, 73.5 mmol) in THF (100 ml) at 0° C. was treated dropwise with n-BuLi (27.3 ml, 2.7 M in hexane, 73.5 mmol), with stirring. After 1 h at 0 to 5° C., the solution was cooled to −40° C., and stirring was continued for 20 min. Dodecyl bromide (17.6 ml) in THF (20 ml) was then added. The mixture came to RT and was stirred for a further 5 h. The reaction was quenched with saturated aqueous $NaHCO_3$ solution (20 ml), and the solution was extracted twice using EtOAc (2×50 ml). The combined organic phases were dried over $NaSO_4$ and concentrated to give a yellow oil. This oil was purified by means of column chromatography (dichloromethane, DCM) to give the desired product 1 (13.8 g, 57.9 mmol, 80%). $^{1}H$ NMR (300 MHz, $CDCl_3$) δ $^{1}H$ ppm: 0.88 (t, 3H, J=6.7 Hz, H-16), 1.20-1.40 (m, 18H), 1.56-1.69 (m, 2H), 2.60 (t, 2H, J=7.6 Hz, H-5), 5.96 (m, 1H, H-3), 6.26 (dd, 1H, J=3.3, 1.9 Hz, H-1), 7.28 (dd, 1H, J=1.7, 0.8 Hz, H-2); $^{13}C$ NMR (75.5 MHz, $CDCl_3$) δ $^{13}C$ ppm: 14.2 (C-16), 22.8, 28.0, 28.1, 29.3, 29.4, 29.5, 29.6, 29.6, 29.7, 29.8, 32.0 (C-5), 104.4 (C-3), 109.9 (C-2), 140.5 (C-1), 156.5 (C-4); (+)-APCI-CID-MS: 237 $[M+H]^+$.

(E)-4-Oxohexadec-2-enal (FIG. 1, 2). A mixture of 2-dodecylfuran (1.00 g, 4.24 mmol) and $NaHCO_3$ (712 mg, 8.48 mmol) in acetone/$H_2O$ (10:1, 2 ml) was treated at −20° C. with NBS (905 mg, 5.11 mmol) dissolved in acetone/$H_2O$ (10 ml). After the mixture had been stirred for 1 h at −20° C., it was treated with pyridine (0.69 ml, 8.48 mmol). Thereafter, the reaction mixture came to RT, and stirring was continued for 2 h. The solution was washed with 1 N HCl, followed by extraction with ethyl acetate (2×50 ml). The organic phase was dried over $NaSO_4$ and concentrated in order to obtain the crude product. The latter was purified by column chromatography (DCM) to give the product as a pale yellow oil (642 mg, 2.55 mmol, 60%). $^{1}H$ NMR (300 MHz, $CDCl_3$) δ $^{1}H$ ppm: 0.88 (t, 3H, J=6.7 Hz, H-16), 1.19-1.36 (m, 18H), 1.59-1.71 (m, H-5), 2.69 (t, 2H, J=7.8 Hz, H-5), 6.73-6.92 (m, 2H, H-2.3), 9.78 (d, CHO, J=7.0 Hz, H-1); $^{13}C$ NMR (75.5 MHz, $CDCl_3$) δ $^{13}C$ ppm: 14.2 (C-16), 22.8, 23.7, 29.2, 29.3, 29.4, 29.5, 29.5, 29.6, 29.7, 32.0, 41.3 (C-5), 137.2 (C-2), 144.8 (C-3), 193.2 (C-1), 199.9 (C-4); (−)-ESI-CID-MS: 251 $[M-H]^-$; ESI-FT-ICR-MS: m/z 251.20137 (calculated for $C_{16}H_{27}O_2^-$, m/z 251.20165).

(E)-4-Oxohexadec-2-enoic acid (FIG. 1, 3). A solution of (E)-4-oxohexadec-2-enal (400 mg, 1.58 mmol) and 2-methyl-2-butene (1.69 ml, 15.8 mmol) in t-BuOH (20 ml) was treated with $NaH_2PO_4$ (2.00 g, 16.7 mmol) and $NaClO_2$ (181 mg, purity 80%, 1.89 mmol), both dissolved in $H_2O$ (10 ml), and the resulting mixture was stirred for 2 h at RT. Most of the solvent was removed under reduced pressure, and EtOAc (50 ml) and a saturated NaCl solution (10 ml) were added to the residue. The aqueous phase was acidified to a pH of 1 by dropwise addition of 1 N HCl. The organic phase was then separated off and the aqueous phase was extracted with EtOAC (2×50 ml). The combined organic phases were dried over NaSO$_4$ and concentrated under reduced pressure to give the product as a whitish-yellow solid (350 mg, 1.31 mmol, 83%), melting point 98±0.5° C. $^1$H NMR (400 MHz, CD$_3$CD$_2$OD) δ $^1$H ppm: 0.87 (t, 3H, J=7.0 Hz, H-16), 1.08-1.34 (m, 18H), 1.56-1.63 (m, 2H), 2.68 (t, 2H, J=7.0 Hz, H-5), 6.65 (d, 1H, J=16.2 Hz, H-2), 7.01 (d, 1H, J=16.2 Hz, H-3); $^{13}$C NMR (100.5 MHz, CD$_3$CD$_2$OD) δ $^{13}$C ppm: 15.5 (C-16), 24.6, 25.7, 26.2, 31.0, 31.3, 31.4, 31.5, 31.6, 31.6, 33.9, 43.0 (C-5), 133.7 (C-2), 141.3 (C-3), 169.4 (C-1), 202.8 (C-4); (−)-ESI-CID-MS: m/z 267 [M−H]$^-$, 535 [2M−H]$^-$; (−)-ESI-CID-MS: m/z 269 [M−H]; ESI-FT-ICR-MS: m/z 267.19633 (calculated for C$_{16}$H$_{27}$O$_3$$^-$, m/z 267.19633).

Sodium (E)-4-oxohexadec-2-enoate (FIG. 1, 4). A solution of (E)-4-oxohexadec-2-enoic acid (115 mg, 0.43 mmol) in THF (100 ml) was treated with NaOH (17.1 mg, 0.43 mmol) dissolved in H$_2$O (5 ml). After 30 min, the pH was measured and brought to 7.5 using NaOH. The solvent was removed under reduced pressure to give a white powder (118 mg, 0.41 mmol, 95%).

P. infestans Culture Conditions.

The isolate 208 m2, which harbors a GFP construct, was used for P. infestans experiments. Zoospoe solutions were prepared by growing P. infestans for 11 days on oat-bean medium at 18° C. in the dark. The mycelium was then flooded with 10 ml of deionized water, left to stand for 4 h at 4° C. to allow the release of the zoospores, and the liquid was then filtered through a layer of gauze to remove pieces of mycelium and sporangia. The solution was adjusted to 1×10$^5$ spores/ml. Sporangia solutions were prepared by flooding mycelium which had been grown for days with 10 ml of deionized water, immediate vigorous shaking to break the sporangia from the sporangiophores and adjusting the solution to 1×10$^4$ sporangia/ml.

P. infestans Bioassays and Infections Experiments.

Spore germination experiments with P. infestans zoosporous solutions were carried out as follows. A dilution series of (E)-4-oxohexadec-2-enoic acid dissolved in 96% strength ethanol was used. The final concentrations in the spore solutions ranged from 10 nM to 100 μM and in each case 2% (v/v) 96% EtOH. Control treatments with 2% (v/v) 96% EtOH only were also carried out. After the treatment, the spores were kept at 4° C. overnight to allow germination. The percentage of germinated spores was calculated after the spores were counted on photographs taken of five nonoverlapping regions of a 10 μl drop in a hematocytometer under a light microscope. The spores were considered to be germinated when the germ tube was at least as long as the spore diameter.

The effect of (E)-4-oxohexadec-2-enoic acid on the mycelial growth of P. infestans was tested by measuring the increase in the GFP fluorescence over time. 24-well microtiter plates (Nunc A/S, Denmark) containing oat-bean medium were inoculated with 100 μl of a P. infestans sporangia solution and grown at 17° C. in the dark. After 24 h, various concentrations of (E)-4-oxohexadec-2-enoic acid were added. The final concentrations (calculated for 100 μl of sporangia solution) ranged from 10 nM to 1 mM and 1% ethanol. The growth of P. infestans was determined by measuring GFP-emitted light (excitation 485 nm, emission 530 nm).

To study the direct effect of (E)-4-oxohexadec-2-enoic acid on live P. infestans mycelium, three-week old mycelium was inoculated dropwise (10 μl) with various concentrations of (E)-4-oxohexadec-2-enoic acid. 24 h later, GFP fluorescence images of inoculated zones were recorded.

Potato plants (Solanum tuberosum L. cv. Désirée) were grown as described. Before an inoculation with a P. infestans zoospore solution, the plants were sprayed to run-off point on the abaxial leaf surface with various concentrations of sodium (E)-4-oxohexadec-2-enoate, dissolved in water. After two hours, when the sprayed leaves had dried, P. infestans was inoculated onto the abaxial leaf surface (six 10 μl drops per leaf; 1×10$^5$ spores/ml; two leaves per plant). The inoculated leaves were then covered with plastic bags to ensure 100% relative atmospheric humidity for spore germination. After three days, the inoculation sites were excised using a cork punch, and all leaf disks of a specific leaf were combined to give one sample. Determinations of the P. infestans biomass were carried out with the aid of quantitative PCR using P. infestans-specific primers.

Colletotrichum coccodes Bioassay.

C. coccodes (CBS369.75) was grown for five days in 50 ml of liquid soybean medium in the dark at 18° C. on a rotary shaker. In order to isolate spores, all of the culture was centrifuged for 5 min at 2100 g and 4° C. The supernatant, which contained the spores, was recentrifuged (10 min, 6500 g, 4° C.). After the supernatant had been decanted off, the pelleted spores were washed carefully in deionized water, centrifuged as above and finally the spore concentration was adjusted to 1×10$^5$ spores/ml in soybean medium. To carry out the biotest, 200 μl of this spore solution were pipetted into each well of a 96-well plate (Nunc A/S, Denmark). The plates were incubated in an incubator for 24 h at 17° C. in the dark to allow germination. Then, test concentrations of (E)-4-oxohexadec-2-enoic acid were pipetted in as described above, with final concentrations of from 0.01 μM to 100 μM and 2% (v/v) ethanol. The plates were returned into the incubator and the increase in fungal biomass was determined by daily OD$_{590}$ measurements.

EXAMPLE 1

Synthesis of (E)-4-oxohexadec-2-enoic acid

A rapid and efficient three-step synthesis of highly bioactive unsaturated fatty acids was developed (FIG. 1). The synthesis of (E)-4-oxohexadec-2-enoic acid (3) starts with a simple 2-alkylation of furan via the deprotonation with n-butyllithium followed by reaction with dodecyl bromide to 2-dodecylfuran (1). The oxidative ring opening of the alkylfuran is performed in the presence of NaHCO$_3$ and NBS in order to generate (E)-4-oxohexadec-2-enal (2). The last step is the oxidation of the aldehyde 2 with NaClO$_2$ in the presence of 2-methyl-2-butene to give (E)-4-oxohexadec-2-enoic acid (3) as chlorine radical scavenger and 1 N HCl (pH=1). The total yield of the three-step process is 35%. To increase the solubility of the compound 3 in water, it is more expedient, for the spraying of plants, to quantitatively form the sodium salt with NaOH.

EXAMPLE 2

P. infestans Spore Germination Assay

To determine the effect of (E)-4-oxohexadec-2-enoic acid (FIG. 1, compound 3) on the spore germination of P. infestans, various concentrations of the compound were adjusted in prepared spore solutions, and the germination rates were determined 24 h later (FIG. 2). Germination was reduced even at very low concentrations (10 nM), by more than 50% compared with the ethanol control at a concentration of 100 nM. At 1 μM, fewer than 10% of the spores germinated, and germination was prevented completely at 3.7 µM. Increasing (E)-4-oxohexadec-2-enoic acid concentrations also had an effect on the length of the germination tubes (FIG. 2*a* to *f*). Furthermore, spore lysis was observed at a concentration of 100 µM (FIG. 2*f*).

EXAMPLE 3

Mycelial Growth of *P. infestans*

The inhibitory effect of (E)-4-oxohexadec-2-enoic acid on the mycelial growth of a GFP-expressing *P. infestans* was studied in a bioassay. Various concentrations were applied to mycelium growing in multiwell plates. GFP fluorescence was recorded with a plate reader to measure the mycelial growth. FIG. 3 shows that growth was inhibited at high concentrations (1 mM).

The effect of (E)-4-oxohexadec-2-enoic acid on mature mycelium was also studied. To this end, test solutions were added dropwise to three-week old mycelium growing on agar plates. FIG. 4 shows that here, too, lower concentrations had a clear negative effect on mycelia viability.

EXAMPLE 4

Infection of Pretreated Plants with *P. infestans*

Furthermore, it was studied whether the pretreatment of potato plants with sodium (E)-4-oxohexadec-2-enoate (FIG. 1, compound 4) has an inhibitory effect on infection with *P. infestans*. To this end, plants grown in a phyto-chamber were sprayed with sodium (E)-4-oxohexadec-2-enoate dissolved in water, two hours before being inoculated with a *P. infestan* zoospore solution. Three days after the inoculation, the growth of *P. infestans* was determined based on the detection of *P. infestans* DNA via quantitative PCR. FIG. 5 shows that pretreatment of the plants with 10 µM and 100 µM of sodium (E)-4-oxohexadec-2-enoate is sufficient to inhibit the infection with *P. infestans* by 80% and 95%, respectively, compared with untreated control plants. Treatment with a very high concentration of 1000 µM sodium (E)-4-oxohexadec-2-enoate had no toxic effects on the leaves.

EXAMPLE 5

Effect of (E)-4-oxohexadec-2-enoic Acid on the Mycelial Growth of *Colletotrichum coccodes*

To determine whether (E)-4-oxohexadec-2-enoic acid also has an inhibitory effect on the ascomycete *c. coccodes*, the causative organism of, inter alia, black dot disease of potato, a multiwell bioassay was set up. The growth of the fungus in liquid medium was determined on the basis of the measurement of the optical density ($OD_{590}$). A medium containing soya was used for this purpose. One-day old mycelium was inoculated together with various concentrations of (E)-4-oxohexadec-2-enoic acid, and the growth of *C. coccodes* was determined every 24 h. As shown in FIG. 6, even low concentrations (0.01 µM) had as significant inhibitory effect on the growth of *C. coccodes*. Increasing concentrations reduced the fungal growth even further. A 1 µM solution of (E)-4-oxohexadec-2-enoic acid inhibited the growth by more than half compared with the ethanol control. 100 µM resulted in complete inhibition.

EXAMPLE 6

Spore Germination Assay Data of Selected Compounds According to the Present Invention

| | | *Phytophthora infestans* (spore germination) | | *Phytophtora infestans* (mycelial growth) | |
|---|---|---|---|---|---|
| Substance | MW g/mol | IC 50 µmol/l | IC 50 µg/ml | IC 50 µmol/l | IC 50 µg/ml |
|  XGL332 | 142.1 | 0.014 | 0.0019 | Not carried out | Not carried out |
|  XGL334 | 170.2 | 0.012 | 0.002 | Not carried out | Not carried out |
|  XGL385 | 170.2 | 0.014 | | Not carried out | Not carried out |

-continued

| Substance | MW g/mol | *Phytophthora infestans* (spore germination) IC 50 µmol/l | IC 50 µg/ml | *Phytophtora infestans* (mycelial growth) IC 50 µmol/l | IC 50 µg/ml |
|---|---|---|---|---|---|
|  DRT276 | 258.3 | 0.07 | 0.018 | 80 | 20.664 |
|  DRT173 | 268.4 | 0.07 | 0.0018 | 450 | 120.78 |
|  XGL384 | 306.5 | 0.06 | 0.018 | Not carried out | Not carried out |
|  XGL388 | 352.5 | 0.1 | 0.035 | Not carried out | Not carried out |

We claim:

1. A method of controlling plant pathogens, comprising applying an effective amount of a compound of formula (I) or a salt thereof, (I)

wherein

X is selected from among H, $OR^1$, $SR^1$, $NR^1R^2$, $N(OR^1)(R^2)$, $N(R^1)—NR^1NR^2$ or $N(R^1R^2R^3)^+A^-$, Y is selected from among $OR^1$, $O^-Cat^+$ or $NR^1R^2$, Z is selected from among O, S, $NR^1$, $NOR^1$, N—CN or $N—NR^1R^2$, R is a substituent selected from the group consisting of (i) an unsubstituted or mono- or polysubstituted ($C_3$-$C_{22}$)-alkyl radical, (ii) an unsubstituted or mono- or polysubstituted ($C_3$-$C_{22}$)-alkenyl radical, (iii) an unsubstituted or mono- or polysubstituted ($C_3$-$C_{22}$)-alkynyl radical, (iv) an unsubstituted or mono- or polysubstituted $—(CH_2)_m$-spermine radical, (v) an unsubstituted or mono- or polysubstituted $—(CH_2)_m$-spermidine radical, (vi) an unsubstituted or mono- or polysubstituted N-methylated $—(CH_2)_m$-sperm(id)ine radical, where m is in each case an integer from 1 to 4 and where the one or the plurality of substituents in the abovementioned radicals (i) to (vi) can be selected independently of one another from among group α, consisting of a ($C_1$-$C_6$)-alkyl radical, a ($C_1$-$C_6$)-thioalkyl radical, a ($C_3$-$C_7$)-cycloalkyl radical which can have one or more hetero atoms such as, for example, O or S, a ($C_1$-$C_6$)-alkoxy radical, a hydroxyl group, a trifluoromethyl group, a triazole group, bromine, chlorine, fluorine, an unsubstituted, mono- or disubstituted phenyl, phenoxy, benzyl, benzyloxy, naphthyl or naphthoxy radical, and (vii) an ethyleneoxy group selected from among:

$—CH_2[OCH_2CH_2]_n—OH$, $—CH_2[OCH_2CH_2]_n—OMe$, $—CH_2—CH_2—[OCH_2CH_2]_n—OH$ $—CH_2—CH_2—[OCH_2CH_2]_n—OMe$ $—CH_2—CH_2—CH_2—[OCH_2CH_2]_n—OH$ $—CH_2—CH_2—CH_2—[OCH_2CH_2]_n—OMe$ $—CH_2—CH_2—CH_2—CH_2—[OCH_2CH_2]_n—OH$ or $—CH_2—CH_2—CH_2—CH_2—[OCH_2CH_2]_n—OMe$, where n=1-20, $R^1$, $R^2$ and $R^3$ independently of one another are selected from the group consisting of hydrogen, a ($C_1$-$C_6$)-acyl radical, $—CONH_2$, $—(CO)—(CH_2)_{0-6}—COOH$, a lactyl radical, a ($C_1$-$C_6$)-alkyl radical, a ($C_3$-$C_7$)-cycloalkyl radical which may contain one or more hetero atoms selected from the group consisting of O and S, an unsubstituted, mono- or disubstituted phenyl, benzyl or naphthyl radical whose substituents can be selected from among group α, A⁻ is an anion selected from among halide, chlorate or carboxylate,
Cat⁺ is a monovalent or divalent cation,
the stereoisomeric center at C5, if present, is present in the R or S form or as a racemate, and
the C2-C3 double bond is present in the E or Z form;
to a plant, a part of the plant or the soil in which the plant grows, wherein the plant pathogenis an oomycete.

2. The method of claim 1, wherein, in formula (I),
X is selected from among H, $OR^1$, $NR^1R^2$, $N(OR^1)(R^2)$, $N(R^1)$—$NR^1R^2$ or $N(R^1R^2R^3)^+A^-$,
Y is selected from among $OR^1$ or $O^-Cat^+$,
Z is selected from among O,
R is a substituent selected from the group consisting of an unsubstituted or mono- or polysubstituted ($C_3$-$C_{22}$)-alkyl radical or an unsubstituted or mono- or polysubstituted ($C_3$-$C_{22}$)-alkenyl radical,
$R^1$, $R^2$ and $R^3$ independently of one another are selected from among hydrogen, a ($C_1$-$C_6$)-acyl radical or a ($C_1$-$C_6$)-alkyl radical, and
the C2-C3 double bond is present in the E form.

3. The method of claim 2, wherein X is $OR^1$ and $R^1$ is hydrogen, a ($C_1$-$C_6$)-acyl radical or a ($C_1$-$C_6$)-alkyl radical.

4. The method of claim 1, wherein R is a ($C_3$-$C_{22}$)-alkyl radical, a ($C_3$-$C_{22}$)-alkenyl radical, —$CH_2[OCH_2CH_2]_n$—OH or —$CH_2[OCH_2CH_2]_n$—OMe, where n=1-20.

5. The method of claim 1, wherein, in formula (I), R is an oligoprenyl radical selected from the groups consisting of geranyl, neryl, farnesyl and geranylgeranyl.

6. The method of claim 1, wherein the compound of the formula (I) is (E)-4-oxohexadec-2-enoic acid or salts thereof.

7. The method of claim 1, wherein the oomycete is selected from the group consisting of the genera *Albugo*, *Bremia*, *Plasmopara*, *Peronospora* and *Phytophthora*.

8. The method of claim 7, wherein the oomycete is *Peronospora manshurica*.

9. The method as claimed in claim 8, wherein the oomycetebelong to the genus *Phytophthora* selected from the group consisting of *Phytophthora sojae*, *Phytophthora palmivora*, *Phytophthora ramorum*, *Phytophthora cinnamomi*, *Phytophthora capsici* and *Phytophthora infestans*.

10. The method as claimed in claim 9, wherein the oomycete is *Phytophthora infestans*.

11. The method as claimed in claim 7, wherein the plant is selected from the group consisting of the Fabaceae; the Cucurbitaceae; the Brassicaceae; the Poaceae; the Solanaceae; *Vitis* spp.; *Beta vulgaris*; and *Theobroma cacao*.

12. The method as claimed in claim 11, wherein the plant is *Solanum tuberosum*.

13. The method as claimed in claim 11, wherein the concentration of the compound of formula (I) or of the salt thereof is from 1 nM to 10 mM.

14. The method of claim 13, wherein, in formula (I),
X is selected from among H, $OR^1$, $NR^1R^2$, $N(OR^1)(R^2)$, $N(R^1)$—$NR^1R^2$ or $N(R^1R^2R^3)^+A^-$,
Y is selected from among $OR^1$ or $O^-Cat^+$,
Z is selected from among O,
R is a substituent selected from the group consisting of an unsubstituted or mono- or polysubstituted ($C_3$-$C_{22}$)-alkyl radical or an unsubstituted or mono- or polysubstituted ($C_3$-$C_{22}$)-alkenyl radical,
$R^1$, $R^2$ and $R^3$ independently of one another are selected from among hydrogen, a ($C_1$-$C_6$)-acyl radical or a ($C_1$-$C_6$)-alkyl radical, and
the C2-C3 double bond is present in the E form.

15. The method of claim 14, wherein X is $OR^1$ and $R^1$ is hydrogen, a ($C_1$-$C_6$)-acyl radical or a ($C_1$-$C_6$)-alkyl radical.

16. The method of claim 13, wherein R is a ($C_3$-$C_{22}$)-alkyl radical, a ($C_3$-$C_{22}$)-alkenyl radical, —$CH_2[OCH_2CH_2]_n$—OH or —$CH_2[OCH_2CH_2]_n$—OMe, where n=1-20.

17. The method of claim 13, wherein, in formula (I), R is an oligoprenyl radical selected from the groups consisting of geranyl, neryl, farnesyl and geranylgeranyl.

18. The method of claim 13, wherein the compound of the formula (I) is (E)-4-oxohexadec-2-enoic acid or salts thereof.

19. The method as claimed in claim 11, wherein
said Fabaceae is *Glycine max;*
said Cucurbitaceae is *Cucurbita* spp., *Cucumis* spp. or *Citrullus* spp.;
said Brassicaceae is *Brassica* spp.;
said Poaceae is *Triticum* spp., *Hordeum* spp., *Oryza* saliva or *Zea mays;*
said Solanaceae is *Nicotiana* spp., *Capsicum* spp., or *Solanum* spp.; or
said *Vitis* spp. is *Vitis vinifera.*

20. The method as claimed in claim 19, wherein
said *Cucurbita* spp. is *Cucurbita pepo;* said *Cucumis* spp. is *Cucumis melo* or *Cucumis sativus;* or
said *Citrullus* spp. is *Citrullus lanatus;*
said *Brassica* spp. is *Brassica napus, Brassica oleracea* or *Brassica rapa;* or
said *Nicotiana* spp. is *Nicotiana tabacum;* said *Capsicum* spp. is *Capsicum annuum,* or said *Solanum* spp. is *Solanum tuberosum, Solanum lycopersicum* or *Solanum melongena.*

* * * * *

UNITED STATES PATENT AND TRADEMARK OFFICE
CERTIFICATE OF CORRECTION

| | | |
|---|---|---|
| PATENT NO. | : 8,648,115 B2 | Page 1 of 1 |
| APPLICATION NO. | : 13/321997 | |
| DATED | : February 11, 2014 | |
| INVENTOR(S) | : Norbert Arnold et al. | |

It is certified that error appears in the above-identified patent and that said Letters Patent is hereby corrected as shown below:

In the Claims

Claim 19:

col. 14, line 34, delete "saliva" and insert therefor --sativa--.

Signed and Sealed this
Seventh Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,648,115 B2  Page 1 of 1
APPLICATION NO. : 13/321997
DATED : February 11, 2014
INVENTOR(S) : Arnold et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 135 days.

Signed and Sealed this

Twenty-ninth Day of September, 2015

Michelle K. Lee
*Director of the United States Patent and Trademark Office*